United States Patent
Yoshida et al.

(10) Patent No.: US 8,999,298 B2
(45) Date of Patent: Apr. 7, 2015

(54) DENTAL ORAL COMPOSITION

(75) Inventors: Yasuhiro Yoshida, Okayama (JP);
Naoko Namba, Okayama (JP);
Noriyuki Nagaoka, Okayama (JP);
Shogo Takashiba, Okayama (JP);
Kazuomi Suzuki, Okayama (JP);
Yamato Nojiri, Kurashiki (JP);
Hiroshige Ishino, Frankfurt (DE);
Takahiro Sekiguchi, Kurashiki (JP);
Koichi Okada, Chiyoda-ku (JP)

(73) Assignee: National University Corporation Okayama University, Okayama-shi (JP)

( * ) Notice: Subject to any disclaimer, the term of this patent is extended or adjusted under 35 U.S.C. 154(b) by 152 days.

(21) Appl. No.: 12/863,330

(22) PCT Filed: Jan. 15, 2009

(86) PCT No.: PCT/JP2009/050476
§ 371 (c)(1),
(2), (4) Date: Jul. 16, 2010

(87) PCT Pub. No.: WO2009/091001
PCT Pub. Date: Jul. 23, 2009

(65) Prior Publication Data
US 2010/0330005 A1 Dec. 30, 2010

(30) Foreign Application Priority Data
Jan. 17, 2008 (JP) .................................. 2008-008428

(51) Int. Cl.
*A61K 8/46* (2006.01)
*A61Q 11/00* (2006.01)
*A61K 8/24* (2006.01)
*A61K 8/55* (2006.01)
*A61K 8/60* (2006.01)
*A61K 8/41* (2006.01)
*A61K 8/73* (2006.01)

(52) U.S. Cl.
CPC . *A61Q 11/00* (2013.01); *A61K 8/24* (2013.01); *A61K 8/55* (2013.01); *A61K 8/60* (2013.01); *A61K 8/416* (2013.01); *A61K 8/602* (2013.01); *A61K 8/73* (2013.01); *A61K 8/732* (2013.01)

(58) Field of Classification Search
None
See application file for complete search history.

(56) References Cited

U.S. PATENT DOCUMENTS

| 5,202,111 A * | 4/1993 | Spaltro et al. .................. 424/49 |
| 5,578,598 A * | 11/1996 | Abe et al. ....................... 514/2.4 |
| 2004/0105823 A1 | 6/2004 | Kamasaka et al. |
| 2008/0038210 A1 * | 2/2008 | Yano et al. ...................... 424/49 |

FOREIGN PATENT DOCUMENTS

| EP | 1 806 125 A1 | 7/2007 |
| EP | 2 044 926 A1 | 4/2009 |
| JP | 7-10726 | 1/1995 |
| JP | 9-175965 | 7/1997 |
| JP | 9-286712 | 11/1997 |
| JP | 2000-154127 | 6/2000 |
| JP | 2005-330269 A | 12/2005 |
| JP | 2006-117574 | 5/2006 |
| WO | WO 2008/010517 A1 | 1/2008 |

OTHER PUBLICATIONS

U.S. Appl. No. 12/374,215, filed Mar. 13, 2009, Yoshida, et al.
U.S. Appl. No. 13/580,573, filed Aug. 22, 2012, Yoshida, et al.
Extended European Search Report issued Oct. 28, 2013, in European Patent Application No. 09701509.3.

* cited by examiner

*Primary Examiner* — Snigdha Maewall
(74) *Attorney, Agent, or Firm* — Oblon, McClelland, Maier & Neustadt, L.L.P.

(57) ABSTRACT

A dental composition for oral use, containing a phosphorylated saccharide (a), a polyphosphoric acid and/or a salt thereof (b), and a cationic bactericidal agent (c), wherein a ratio of a total amount of the phosphorylated saccharide (a) and the polyphosphoric acid and/or a salt thereof (b) contained to an amount of the cationic bactericidal agent (c) contained, i.e. {(a)+(b)}/(c), is from 0.05 to 20 in a weight ratio. The dental composition for oral use of the present invention can be suitably used for an oral cavity cleaning agent, including dentifrice agents such as a paste dentifrice agent, a powder dentifrice agent, and a liquid dentifrice agent, a mouse-wash agent, a troche, a tablet, a cream, an ointment, a bonding agent, a mouth spray, a coating agent to tooth surface or a dental prosthetic, a hypersensitive inhibitor, a therapeutic agent for periodontal diseases, that is applied to a periodontal pocket, wet tissue for oral cavity care, an oral refreshing agent, chewing gum, or a gargling agent, or the like.

6 Claims, No Drawings

DENTAL ORAL COMPOSITION

CROSS-REFERENCE TO RELATED APPLICATIONS

This application is a National Stage of PCT/JP09/050476 filed Jan. 15, 2009 and claims the benefit of JP 2008-008428 filed Jan. 17, 2008.

TECHNICAL FIELD

The present invention relates to a dental composition for oral use. More specifically, the present invention relates to a dental composition for oral use capable of suppressing bacterial adhesion to teeth and mucosal membrane surface in the oral cavity, whereby consequently being capable of suppressing the formation of dental plaques and dental calculi on the surface of the teeth, and further being useful as prophylactic materials for dental caries, periodontal diseases, and halitosis.

BACKGROUND ART

Diseases in the oral cavity include dental caries, periodontal diseases, such as gingivitis and periodontitis, stomatitis, and the like. Among them, the dental caries is a representative disease of teeth, which is developed due to the dissolution of dentine by an acid produced by microorganisms in the oral cavity. Among the microorganisms in the oral cavity, *Streptococcus mutans*, which may be hereinafter simply referred to as *S. mutans*, is considered as one of the pathogenic bacteria for dental caries. In addition, the periodontitis which is an inflammatory disease of a periodontal tissue is said to be developed due to the bacteria in the oral cavity. In general, if the bacteria causing dental caries as described above are adhered to the surfaces of the teeth, the dental plaques are formed, which are said to be causative of various diseases in the oral cavity, such as dental caries and periodontal diseases.

For this reason, a dental composition for oral use which applies the technique of coating surfaces of the teeth with a specified drug or a polymer, thereby suppressing the adhesion of bacteria, to inhibit the formation of plaques has been proposed. Among them, a composition containing a cationic bactericidal agent, such as cetyl pyridinium chloride, benzethonium chloride, or chlorhexidine, the composition having a high bactericidal activity against bacteria in the oral cavity has been well used for this purpose. However, the cationic bactericidal agent as described above cannot be detained on the surfaces of the teeth for a long time when used alone, so that the agent has disadvantages such as lowered sustainability of the effects, thereby making it poor in actual use.

In order to solve the problems as mentioned above, for example, a technique of accelerating an adsorption action of a bactericidal agent by using a lower alkyl ester of an N-long-chained acyl basic amino acids in combination with a cationic bactericidal agent (see, for example, Patent Publication 1), a technique of using a polyphosphoric acid and a polyglycerol fatty acid ester in combination with a cationic bactericidal agent (see, for example, Patent Publication 2), and a technique of using a polymer of ammonium dimethyldiallyl chloride as a cationic bactericidal agent (see, for example, Patent Publication 3) have been disclosed.

Patent Publication 1: Japanese Patent Laid-Open No. Hei 9-286712
Patent Publication 2: Japanese Patent Laid-Open No. 2006-117574
Patent Publication 3: Japanese Patent Laid-Open No. Hei 9-175965

DISCLOSURE OF INVENTION

Problems to be Solved by the Invention

In order to exhibit an effect of suppressing bacterial adhesion even in according to the conventional techniques, since the compositional ratio of the bactericidal agent in the composition must be made into a relatively high concentration, a disadvantage in safety of live body is likely to be caused, and the residual property of the bactericidal agent on the surfaces of the teeth is not yet sufficient, thereby giving rise to a disadvantage that it is difficult to allow the effect to last. Therefore, the development of a dental composition for oral use so as to be capable of effectively inhibiting the adhesion of bacteria in the oral cavity to the surfaces of the teeth by a convenient method, and allowing the effect to last for a long time period has been desired.

Means to Solve the Problems

The present invention has been accomplished in view of meeting the above needs, and the present invention relates to a dental composition for oral use which is capable of suppressing the adhesion of the bacteria in the oral cavity to surfaces of the teeth for a long time period by enhancing the residual property of a cationic bactericidal agent to the surfaces. Also, the present invention relates to a dental composition for oral use having excellent safety of live body that is capable of effectively suppressing the bacterial adhesion with a bactericidal agent in an even smaller formulation amount.

The present inventors have found that a phosphorylated saccharide and a polyphosphoric acid are combined, thereby accelerating the adsorption of a cationic bactericidal agent to surfaces of the teeth and at the same time enhancing the residual property on the surfaces. The present invention has been perfected thereby.

Specifically, the gist of the present invention relates to a dental composition for oral use, containing a phosphorylated saccharide (a), a polyphosphoric acid and/or a salt thereof (b), and a cationic bactericidal agent (c) in a particular ratio.

Effects of the Invention

When a dental composition for oral use of the present invention is used, the adhesion of bacteria in the oral cavity to surfaces of the teeth can be suppressed for a long period of time, so that the plaques and the dental calculi are less likely to be adhered to the surfaces of the teeth, thereby contributing to the prevention of dental caries, periodontal diseases, halitosis, aspiration pneumonia, or the like. Also, when the composition is applied to a periodontal pocket, plaques are less likely to be formed in a gap between the teeth and the gingivae, thereby contributing to the prevention and the treatment of periodontal diseases. In addition, since the composition of the present invention exhibits a high effect even with a smaller amount of a bactericidal agent formulated in the composition, the composition also has excellent safety upon the use of the composition of the present invention in the oral cavity.

BEST MODE FOR CARRYING OUT THE INVENTION

The present invention will be described more specifically hereinbelow.

The dental composition for oral use of the present invention contains a phosphorylated saccharide (a), a polyphosphoric acid and/or a salt thereof (b), and a cationic bactericidal agent (c) in a particular ratio.

The phosphorylated saccharide (a) in the dental composition for oral use of the present invention is used for the purposes of accelerating the adsorption of a cationic bactericidal agent (c) to surfaces of the teeth and enhancing the residual property on the surfaces. The phosphorylated saccharide includes, for example, those obtained by subjecting a part or all of hydroxyl groups of monosaccharides, polysaccharides, and sugar alcohols to phosphorylation. In the above phosphorylated saccharide (a), a part or all of the phosphorylated saccharide may be in the form of salts. These salts are exemplified by sodium salts, potassium salts, calcium salts, magnesium salts, ammonium salts, and the like.

The monosaccharide includes, for example, glucose, galactose, fructose, mannose, xylose, arabinose, ribose, and the like. The polysaccharide includes, for example, lactose, sucrose, sucralose, cellobiose, trehalose, maltose, Palatinose (registered trademark), maltotriose, maltodextrin, cyclodextrin, glycosylsucrose, amylose, amylopectin, cycloamylose, glycogen, cellulose, agarose, cluster dextrin, mannan, pullulan, and the like. The sugar alcohol includes, for example, glycerol, erythritol, pentaerythritol, dipentaerythritol, arabitol, ribitol, xylitol, sorbitol, mannitol, galactitol, maltitol, lactitol, Palatinitol (registered trademark), inositol, quercitol, and the like.

The phosphorylated saccharide usable in the dental composition for oral use of the present invention can be produced according to a known method by subjecting a hydroxyl group of at least one saccharide selected from the group consisting of the monosaccharides, the polysaccharides, and the sugar alcohols as mentioned above to phosphorylation. For example, a method of reacting with sodium metaphosphate described in *Carbohydrate Research* 302 (1997), 27-34, a method of reacting with sodium phosphate described in Japanese Patent Laid-Open Nos. 2005-330269 and 2005-330270, and the like are used. Furthermore, as described in WO 87/07142, a method of reacting phosphorus pentoxide and pullulan to give phosphorylated pullulan is preferably used.

As the phosphorylated saccharide usable in the dental composition for oral use of the present invention, those obtained by subjecting a part or all of the hydroxyl groups of at least one saccharide selected from the group consisting of the monosaccharides, the polysaccharides, and the sugar alcohols as mentioned above to phosphorylation can be used. The phosphorylated saccharide includes, for example, phosphorylated glucose (for example, glucose-6-phosphoric acid), phosphorylated galactose, phosphorylated fructose, phosphorylated mannose, phosphorylated xylose, phosphorylated arabinose, phosphorylated ribose, phosphorylated lactose, phosphorylated sucrose, phosphorylated sucralose, phosphorylated cellobiose, phosphorylated trehalose, phosphorylated maltose, phosphorylated Palatinose, phosphorylated maltotriose, phosphorylated maltodextrin, phosphorylated cyclodextrin, phosphorylated glycosylsucrose, phosphorylated amylose, phosphorylated amylopectin, phosphorylated cycloamylose, phosphorylated glycogen, phosphorylated cellulose, phosphorylated agarose, phosphorylated cluster dextrin, phosphorylated mannan, phosphorylated pullulan, phosphorylated glycerol, phosphorylated erythritol, phosphorylated pentaerythritol, phosphorylated dipentaerythritol, phosphorylated arabitol, phosphorylated ribitol, phosphorylated xylitol, phosphorylated sorbitol, phosphorylated mannitol, phosphorylated galactitol, phosphorylated maltitol, phosphorylated lactitol, phosphorylated Palatinitol, phosphorylated inositol, phosphorylated quercitol, and the like.

Among these phosphorylated saccharides, the phosphorylated polysaccharides having a number-average molecular weight Mn of preferably from 1,000 to 100,000 is preferred, from the viewpoint of the effect of suppressing adhesion of bacteria, the production cost, and storage stability, and the like, and, for example, one or more members selected from the group consisting of phosphorylated maltodextrin, phosphorylated cyclodextrin, phosphorylated glycosylsucrose, phosphorylated amylose, phosphorylated amylopectin, phosphorylated cycloamylose, phosphorylated glycogen, phosphorylated cellulose, phosphorylated agarose, phosphorylated cluster dextrin, phosphorylated mannan, and phosphorylated pullulan are preferred. Further, the phosphorylated pullulan is more preferred, from the viewpoint of being less likely to be metabolized with amylase or the like in the oral cavity, thereby making it less likely to serve as a nutrient for bacteria. Here, when the phosphorylated polysaccharide has a number-average molecular weight Mn of less than 1,000, it is undesirable in the dental composition for oral use of the present invention because the phosphorylated polysaccharide is less likely to act to bind to a bactericidal agent, or adsorption strength of a complex of the bactericidal agent and the phosphorylated polysaccharide to the surfaces of the teeth is weakened, which in turn has a risk of lowering the effect of suppressing adhesion of bacteria of dental caries. On the other hand, when the phosphorylated polysaccharide has the molecular weight exceeding 100,000, it is undesirable because a solubility in a solvent is lowered and viscosity of the composition increases, which in turn has a risk that leads to cause poor operability. In the present invention, the preferred phosphorylated polysaccharide has a number-average molecular weight Mn in the range of from 1,000 to 100,000, more preferably from 2,000 to 70,000, even more preferably from 5,000 to 50,000, and even more preferably from 10,000 to 30,000.

It is desired that the phosphorylated saccharide suitably used in the dental composition for oral use of the present invention is one in which hydroxyl groups of the saccharide are phosphorylated in an amount of preferably from 0.5 to 15% by number, and more preferably from 2 to 10% by number, of the hydroxyl groups of the saccharide. Here, the number ratio of the hydroxyl groups that are phosphorylated in the phosphorylated saccharide can be calculated by measuring an amount of phosphorus contained by performing elemental analysis of the phosphorylated saccharide, and obtaining the ratio assuming that all the measured phosphorus are derived from the hydroxyl groups that are subjected to phosphorylation.

The polyphosphoric acid and/or a salt thereof (b) in the dental composition for oral use of the present invention is also used for the purpose of accelerating adsorption of a cationic bactericidal agent (c) to the surface of the teeth, and enhancing residual property on the surface. The polyphosphoric acid of the present invention may be partly or entirely in the form of a salt. The polyphosphoric acid usable in the present invention is not particularly limited, and includes a linear polyphosphoric acid obtainable by subjecting orthophosphoric acid to dehydration condensation, a cyclic polyphosphoric acid, a polyphosphoric acid which is irregularly connected in a network manner, and the like. Examples of the linear polyphosphoric acid are pyrophosphoric acid, tripolyphosphoric acid, tetrapolyphosphoric acid, pentapolyphosphoric acid, hexapolyphosphoric acid, and the like. Examples of the cyclic polyphosphoric acid are trimetaphosphoric acid, tetrametaphosphoric acid, hexametaphosphoric acid, and the like. Further, an example of the polyphosphoric acid which is irregularly connected in a network manner is ultrapolyphosphoric acid. As the salts of the polyphosphoric acid, an alkali metal salt, such as a sodium salt or a potassium salt, an acidic condensed phosphate salt, which is a mixed salt of an alkali metal ion and a hydrogen ion, an ammonium salt or the like is preferably used. The alkali metal salt is preferred from the viewpoint of convenience in use.

The polyphosphoric acid and/or a salt thereof in the present invention, as shown in Comparative Examples described later, is not found to have any effects on accelerating adsorption of the cationic bactericidal agent to the surface of the teeth when used alone, or if found to have any effects, very little; however, when used together with the component (a), a phosphorylated saccharide, its function becomes remarkable. Although its mechanism is not fully elucidated, the present inventors have deduced it to be as follows. Specifically, a polyphosphoric acid and/or a salt thereof and a phosphorylated saccharide (hereinafter, both are being simply referred to as phosphoric acid group-containing compound) have a phosphoric acid group in the molecule, and the phosphoric acid group has a high affinity with hydroxyapatite, a main ingredient of the dentine, so that the phosphoric acid group-containing compound is more likely to adsorb to the surface of the teeth and be held thereto. The cationic bactericidal agent is presumably electrostatically or physically held via a phosphoric acid group-containing compound adsorbed to the surface of the teeth, and to which extent the phosphoric acid group-containing compound is adsorbed to the surface of the teeth would be important in exhibiting the effects of the present invention. (Here, the phrase "cationic bactericidal agent is electrostatically held" means a state in which mainly an anionic phosphoric acid group-containing compound and a cationic bactericidal agent are electrostatically allowed to form a complex, thereby adsorbing the cationic bactericidal agent to the surface of the teeth in the form of the complex; on the other hand, the phrase "cationic bactericidal agent is physically held" means a state in which a cationic bactericidal agent is held by intertwining with a chained phosphoric acid group-containing compound.)

All the phosphoric acid group-containing compounds have a phosphoric acid group, and the compounds can be adsorbed to the surface of the teeth, and further can electrostatically hold a cationic bactericidal agent. However, since the physical holding is exhibited by intertwining a cationic bactericidal agent with a molecular chain of the phosphoric acid group-containing compound, sufficient holding effects may not be exhibited in some cases depending on the length of the molecular chain. For this reason, it is deduced that sufficient effects are not observed on the physical holding when a polyphosphoric acid and/or salt thereof having a short molecular chain length is used alone.

On the other hand, when the physical holding of the cationic bactericidal agent is expected, it is considered to be helpful to use a phosphorylated saccharide having a long molecular chain, and preferably a phosphorylated polysaccharide. However, the phosphorylated saccharide alone cannot be said to be sufficient at all in electrostatic holding of the bactericidal agent because of the proportion of the phosphoric acid group within the molecule, and if the phosphorylated saccharide is blended in excess, the cationic bactericidal agent would be embedded in the phosphorylated saccharide, thereby making it likely to weaken its effect.

In view of the above, it is deduced that a component excellent in electrostatic holding, such as a polyphosphoric acid and a component excellent in physical holding such as a phosphorylated saccharide are used together, so that the balance between the electrostatic holding and the physical holding is optimized, thereby making it possible to specifically detain the cationic bactericidal agent to the surface of the teeth, and sustain its function.

The cationic bactericidal agent (c) usable in the dental composition for oral use of the present invention is a compound having a bactericidal action against the bacteria in the oral cavity, and the cationic bactericidal agent includes, for example, a quaternary ammonium salt represented by the following general formula (I):

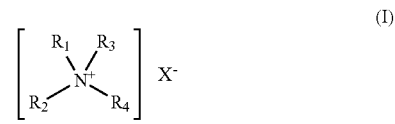

(I)

wherein each of $R_1$, $R_2$, $R_3$, and $R_4$ is independently a substituted or unsubstituted, saturated or unsaturated, and branched or linear aliphatic group having 1 to 30 carbon atoms, for example, an alkyl group, an arylalkyl group, an alkoxyalkyl group, a polyoxyalkyl group, an alkylamide alkyl group, an alkylsulfamide alkyl group, a hydroxyalkyl group, a halogen atom-substituted alkyl group, or the like; or an aromatic group, for example, an aryl, an alkylaryl or the like, or two or three of any of $R_1$, $R_2$, $R_3$, and $R_4$ may be connected to form a ring; and $X^-$ is an anion selected from the group consisting of a halide (including, for example, a chloride, a bromide, and an iodide), an acetate, a citrate, a lactate, a glycolate, a phosphate, a nitrate, a sulfate, an alkyl sulfate, an aryl sulfate, an alkylaryl sulfate, a perchlorate, and a tetrafluoroborate.

Specific examples of the compounds of the general formula (I) include dodecyltrimethylammonium chloride, tetradecyltrimethylammonium chloride, hexadecyltrimethylammonium chloride, octadecyltrimethylammonium chloride, dodecyldimethylbenzylammonium chloride, tetradecyldimethylbenzylammonium chloride, hexadecyldimethylbenzylammonium chloride, octadecyldimethylbenzylammonium chloride, octadecyldimethylbenzylammonium bromide, octadecyldimethylbenzylammonium iodide, (dodecylphenylmethyl)trimethylammonium chloride, dioctadecyldimethylammonium chloride, dioctadecyldibenzylammonium chloride, trioctadecylbenzyl ammonium chloride, octadecyltrihydroxyethylammonium chloride, and the like. In addition, examples of the compounds of the general formula (I) include the following compounds.

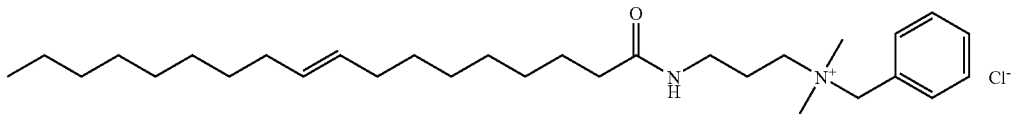

-continued

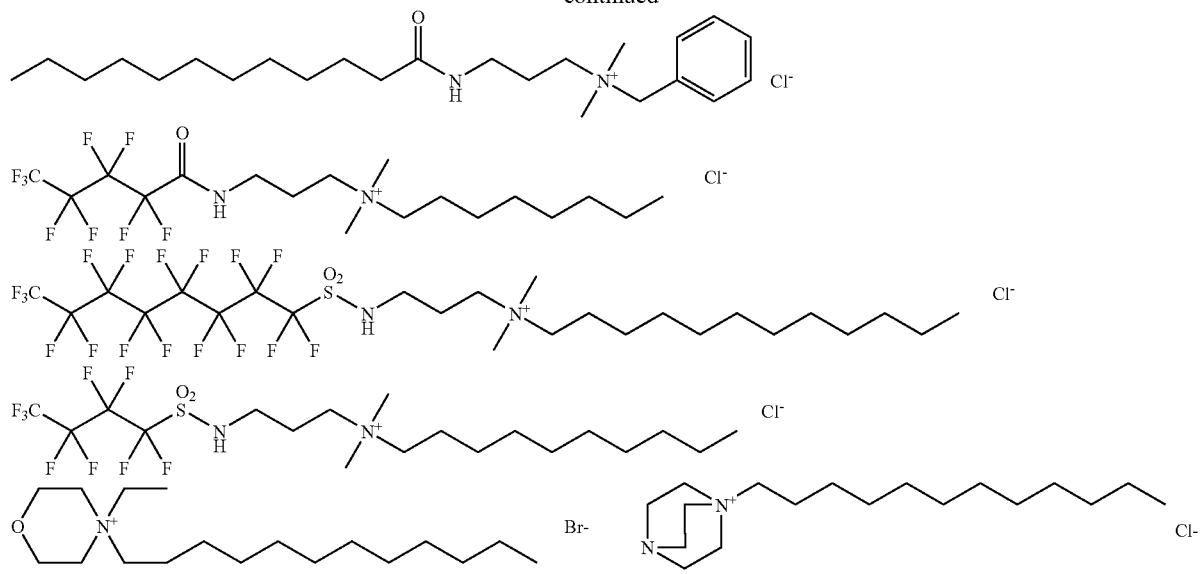

In addition, the cationic bactericidal agent usable in the dental composition for oral use of the present invention includes a quaternary ammonium salt represented by the following general formula (II):

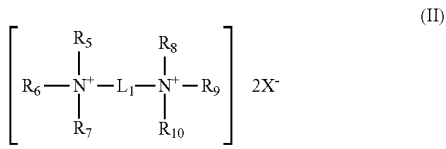

wherein each of $R_5$, $R_6$, $R_7$, $R_8$, $R_9$, and $R_{10}$ is independently a substituted or unsubstituted, saturated or unsaturated, and branched or linear aliphatic group having 1 to 30 carbon atoms, for example, an alkyl group, an arylalkyl group, an alkoxyalkyl group, a polyoxyalkyl group, an alkylamide alkyl group, an alkylsulfamide alkyl group, a hydroxyalkyl group, a halogen atom-substituted alkyl group, or the like; or an aromatic group, for example, an aryl, an alkylaryl or the like, or two or three of any of $R_5$, $R_6$, $R_7$, $R_8$, $R_9$, and $R_{10}$ may be connected to form a ring;

$L_1$ is a substituted or unsubstituted divalent linking group, for example, an alkylene group, an arylene group, or an arylalkylene group; and $X^-$ is an anion selected from the group consisting of a halide (for example, a chloride, a bromide, and an iodide), an acetate, a citrate, a lactate, a glycolate, a phosphate, a nitrate, a sulfate, an alkyl sulfate, an aryl sulfate, an alkylaryl sulfate, a perchlorate, and a tetrafluoroborate.

Specific examples of the compounds of the general formula (II) include a compound represented by the following general formula (III):

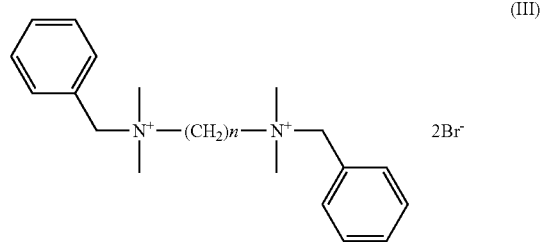

wherein n is an integer of from 2 to 12, and the following compounds, and the like.

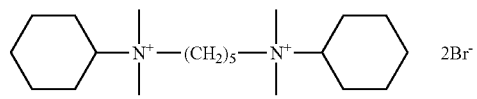 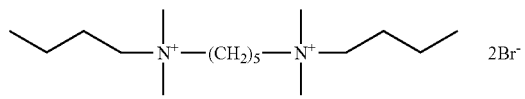

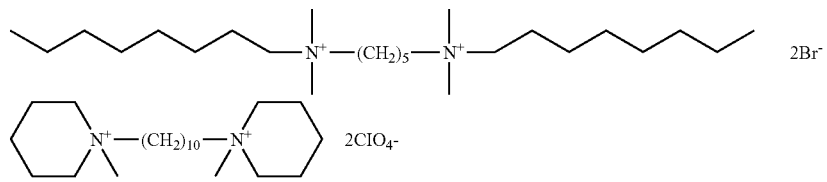

In addition, the cationic bactericidal agent usable in the dental composition for oral use of the present invention includes a quaternary ammonium salt represented by the following general formula (IV):

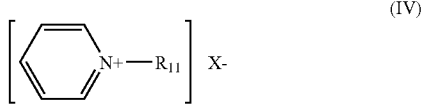
(IV)

wherein $R_{11}$ is a substituted or unsubstituted, saturated or unsaturated, and branched or linear aliphatic group having 1 to 30 carbon atoms, for example, an alkyl group, an arylalkyl group, an alkoxyalkyl group, a polyoxyalkyl group, an alkylamide alkyl group, an alkylsulfamide alkyl group, a hydroxyalkyl group, a halogen atom-substituted alkyl group, or the like; or an aromatic group, for example, an aryl, an alkylaryl, or the like; and $X^-$ is an anion selected from the group consisting of a halide (for example, a chloride, a bromide, and an iodide), an acetate, a citrate, a lactate, a glycolate, a phosphate, a nitrate, a sulfate, an alkyl sulfate, an aryl sulfate, an alkylaryl sulfate, a perchlorate, and a tetrafluoroborate.

Specific examples of the compounds of the general formula (IV) include dodecylpyridinium chloride, tetradecylpyridinium chloride, cetylpyridinium chloride, 12-methacryloyloxydodecylpyridinium bromide, and the like. Also, examples of the compounds of the general formula (IV) include the following compounds.

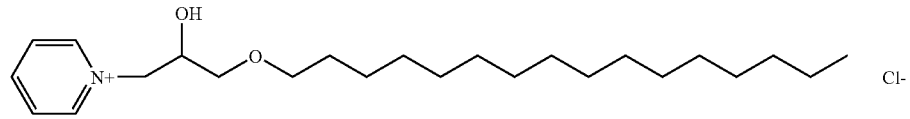

In addition, the cationic bactericidal agent usable in the dental composition for oral use of the present invention includes a pyridinium salt represented by the following general formula (V):

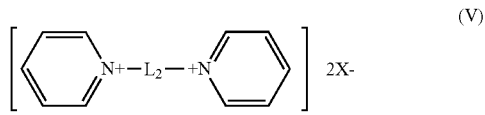
(V)

wherein $L_2$ is a substituted or unsubstituted divalent linking group, for example, an alkylene group, an arylene group, or an arylalkylene group; and $X^-$ is an anion selected from the group consisting of a halide (for example, a chloride, a bromide, and an iodide), an acetate, a citrate, a lactate, a glycolate, a phosphate, a nitrate, a sulfate, an alkyl sulfate, an aryl sulfate, an alkylaryl sulfate, a perchlorate, and a tetrafluoroborate.

Specific examples of the compounds of the general formula (V) include a compound represented by the following general formula (VI):

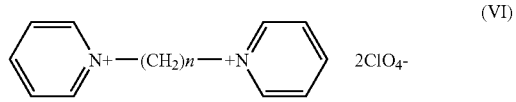
(VI)

wherein n is an integer of from 2 to 12.

In addition, the cationic bactericidal agent usable in the dental composition for oral use of the present invention includes a quaternary ammonium salt represented by the following general formula (VII):

(VII)

$$\left[\begin{array}{c} R_{12} \\ | \\ N \\ \diagup \diagdown \\ \diagdown \diagup \\ N^+ \\ | \\ R_{13} \end{array}\right] X^-$$

wherein each of $R_{12}$ and $R_{13}$ is independently a substituted or unsubstituted, saturated or unsaturated, and branched or linear aliphatic group having 1 to 30 carbon atoms, for example, an alkyl group, an arylalkyl group, an alkoxyalkyl group, a polyoxyalkyl group, an alkylamide alkyl group, an alkylsulfamide alkyl group, a hydroxyalkyl group, a halogen atom-substituted alkyl group, or the like; or an aromatic group, for example, an aryl, an alkylaryl or the like; and $X^-$ is an anion selected from the group consisting of a halide (for example, a chloride, a bromide, and an iodide), an acetate, a citrate, a lactate, a glycolate, a phosphate, a nitrate, a sulfate, an alkyl sulfate, an aryl sulfate, an alkylaryl sulfate, a perchlorate, and a tetrafluoroborate.

Specific examples of the compounds of the general formula (VII) include the following compound.

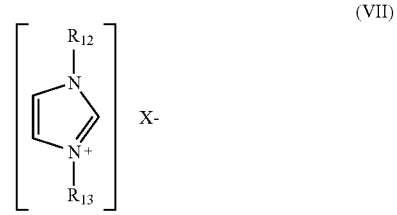

Among these cationic bactericidal agents represented by the above general formulas, those compounds in which each of $R_1$ to $R_{13}$, which is a substituent on a nitrogen atom in any of the above general formulas, is independently a substituted or unsubstituted, saturated or unsaturated, and branched or linear alkyl group or arylalkyl group are preferred, and those in which the substituent is an unsubstituted, saturated or unsaturated, and branched or linear alkyl group or arylalkyl group are more preferred, and those in which the substituent is an unsubstituted, saturated, linear alkyl group or arylalkyl group are even more preferred, from the viewpoint of improving detainability of the bactericidal agent in the oral cavity.

In addition, among these cationic bactericidal agents represented by the above general formulas, when consideration is made in the aspect that the dental composition for oral use of the present invention is used in the oral cavity, of these cationic bactericidal agents, it is preferable to use a quaternary ammonium salt represented by the above-mentioned general formula (I) and a quaternary ammonium salt represented by the above-mentioned general formula (IV), from the viewpoint of a balance between the safety and the bactericidal effects.

Among the compounds represented by the general formulas (I) and (IV) mentioned above, compounds having a critical micelle concentration of 10 mM or lower are preferably used, and compounds having a critical micelle concentration of 1 mM or lower are more preferably used, and compounds having a critical micelle concentration of 0.001 to 0.5 mM are even more preferably used. Specifically, a compound which is a chloride or a phosphate, in which at least one of $R_1$, $R_7$, $R_3$, and $R_4$, or $R_{11}$ has 12 or more carbon atoms is preferred. The compound as described above includes octadecyltrimethylammonium chloride, tetradecyldimethylbenzylammonium chloride, octadecyldimethylbenzylammonium chloride, cetylpyridinium chloride, and the like, and octadecyldimethylbenzylammonium chloride and cetylpyridinium chloride are preferred.

Besides those listed above, cationic surfactants including commercially available products described in, for example, "13398 no Kagaku Shohin (13398 Chemical Commercial Products) (The Chemical Daily Co., Ltd., Japan)," pages 1203-1205, "Handbook of Industrial Surfactants, 2nd Edition, Vol. 2" (Gower), "Surfactant systems" (Chapman and hall), "Industrial surfactants" (NOYES), "Shin-ban Kaimen Kasseizai Handbook (New Edition Surfactant Handbook)" (Kougakutosho Ltd.), or the like can be used. Commercially available products are quaternary ammonium salts of fatty acids, benzalkonium salts, benzethonium chloride, pyridinium salts, imidazolinium salts, and the like, and the quaternary ammonium salts of fatty acids, the benzalkonium salts, and benzethonium chloride can be preferably used, and the benzalkonium salts can be more preferably used. Commercially available benzalkonium salts include CATION F2-35R, CATION F2-40E, CATION F2-50, CATION F2-50E (hereinabove, manufactured by NOF CORPORATION), ARQUAD CB-50 (manufactured by Lion), CATIOGEN S, CATIOGEN TMS-C (hereinabove, manufactured by DAI-ICHI KOGYO SEIYAKU CO., LTD.), TEXNOL (manufactured by Nippon Nyukazai Co., Ltd.), and the like.

The use of the cationic bactericidal agent is not limited to a single kind, but plural cationic bactericidal agents may be mixed in a given ratio. In addition, a commercially available cationic bactericidal agent, which is a mixture of plural compounds due to difference in alkyl groups and the like may be used.

The dental composition for oral use of the present invention can further contain a solvent (d). The solvent (d) usable in the dental composition for oral use of the present invention refers to a liquid having a boiling point within the range of from 40° to 180° C. at an ambient pressure (101.3 kPa), and the solvent includes, for example, water; alcohols such as methanol, ethanol, isopropanol, n-propanol, butanol, and cyclohexanol; halogenated solvents such as chloroform, methylene chloride, and chlorobenzene; hydrocarbons such as hexane, cyclohexane, toluene, and xylene; ketones such as acetone, methyl ethyl ketone, and cyclohexanone; esters such as ethyl acetate and butyl acetate; ethers; and the like, and the solvent is not limited to those exemplified above. However, in consideration of the fact that the dental composition for oral use of the present invention is mainly used in the oral cavity in most cases, among these solvents, water and ethanol are preferred. In addition, water and ethanol may be properly mixed in a given ratio and used.

In the dental composition for oral use of the present invention, the phosphorylated saccharide (a) is contained in an amount of preferably from 0.001 to 10% by weight, more preferably from 0.005 to 2% by weight, and even more preferably from 0.01 to 1% by weight, of the composition, from the viewpoint of detaining the cationic bactericidal agent on the surfaces of the teeth more effectively.

The polyphosphoric acid and/or a salt thereof (b) is also contained in an amount of preferably from 0.001 to 10% by weight, more preferably from 0.005 to 2% by weight, and even more preferably from 0.01 to 1% by weight, of the composition, from the viewpoint of detaining the cationic bactericidal agent on the surfaces of the teeth more effectively.

The cationic bactericidal agent (c) is contained in an amount of preferably from 0.0001 to 5% by weight, more preferably from 0.0005 to 2% by weight, and even more preferably from 0.001 to 1% by weight, of the composition, from the viewpoint of balance between safety and bactericidal effect and lastingness of the bactericidal effect.

The solvent (d) is contained in an amount of preferably from 50 to 99.9979% by weight, more preferably from 70 to 99.9979% by weight, and even more preferably from 90 to 99.9979% by weight, of the composition, from the viewpoint of providing the composition with an excellent operability and homogeneously dissolving the bactericidal agent and the phosphorylated saccharide.

When the phosphoric acid group-containing compounds are contained in excess, an electric repulsion is caused between the phosphoric acid group-containing compounds themselves, thereby making it difficult to hold a sufficient amount of a cationic bactericidal agent on the surfaces of the teeth. On the other hand, when the cationic bactericidal agent is contained in excess, the adsorption to the surfaces of the teeth is weakened due to the presence of a positively charged cationic bactericidal agent in the surrounding of the phosphoric acid groups of the phosphoric acid group-containing compounds. From the viewpoints as described above, a ratio of a total amount of the phosphorylated saccharide (a) and the polyphosphoric acid and/or a salt thereof (b) contained to an amount of the cationic bactericidal agent (c) contained, i.e. {(a)+(b)}/(c) (weight ratio), is within the range of from 0.05 to 20, and preferably within the range of from 0.1 to 10, more preferably from 0.2 to 5, and even more preferably from 0.5 to 2. In addition, supposing that a total sum of (a), (b), and (c) is 1 part by weight, the solvent (d) is contained in an amount of preferably within the range of from 1 to 49,999 parts by weight, and more preferably within the range of from 100 to 10,000 parts by weight.

In addition, a ratio of the amounts of the phosphorylated saccharide (a) to the polyphosphoric acid and/or a salt thereof (b) contained, i.e. (a)/(b) (weight ratio), is preferably within the range of from 0.001 to 1000, more preferably from 0.02 to 50, even more preferably from 0.1 to 10, and even more preferably from 0.2 to 5.

Since the dental composition for oral use of the present invention is assumed to be used in the oral cavity, it is desired that the dental composition for oral use has a pH near neutrality. In addition, it is desired that the dental composition for oral use of the present invention has a pH range adjusted to preferably from 4 to 9, more preferably from 5 to 8, and even more preferably from 6 to 7.5, from the viewpoint of maximally exhibiting the effect of the bactericidal agent contained in the dental composition for oral use of the present invention. The pH of the dental composition for oral use of the present invention can be adjusted depending upon the kinds of the phosphorylated saccharide (a), the polyphosphoric acid and/or a salt thereof (b), and the cationic bactericidal agent (c) used, and their respective formulation ratio and concentrations. Also, a pH adjusting agent may be further added thereto. As the pH adjusting agent, a known one can be used without any limitations, and the agent includes, for example, organic acids such as acetic acid, citric acid, DL-malic acid, succinic acid, and fatty acids and salts thereof; carbonates such as sodium carbonate and calcium carbonate; phosphoric acids such as phosphoric acid and salts thereof; various amino acids such as glycine, alanine, aspartic acid, and glutamic acid and salts thereof; and amines such as triethanolamine.

Further, the dental composition for oral use of the present invention can contain a flavor, a nonionic surfactant, an anionic surfactant, a viscosity adjusting agent, a polyhydric alcohol, a buffering agent, other pharmaceutically effective agent, a sweetener, a colorant, an antioxidant, an abrasive, or the like, as occasion demands.

As an example of the flavor, an oil-soluble flavor is preferably used. The flavor including, for example, not only a synthetic flavor such as menthol, carvone, anethole, eugenol, cineol, thymol, methyl salicylate, pulegone, menthone, pinene, limonene, or menthyl acetate, but also a natural purified oil, such as a mint oil, such as peppermint oil, spearmint oil, or Japanese mint oil, a citrus oil, such as lemon, orange, grapefruit, or lime, and a herb oil, such as eucalyptus, sage, rosemary, thyme, laurel, basil, labiate, bay, estragon, parsley, celery, or coriander, a spice oil, such as cinnamon, pepper, nutmeg, mace, clove, ginger, cardamon, or anise; or a fruit flavor, such as apple, banana, melon, grape, peach, strawberry, blueberry, raspberry, black currant, litchi, star fruit, passion fruit, plum, pineapple, or muscat, or the like can be suitably used. Among these oil-soluble flavors, menthol, carvone, peppermint oil, spearmint oil, Japanese mint oil, methyl salicylate, cineol, limonene, and pinene are more preferred, from the viewpoint of giving a refreshing taste and savoriness to the oral cavity. These oil-soluble flavors can be used singly or in a combination of two or more kinds. It is desired that each of these oil-soluble flavors is contained in an amount of preferably from 0.1 to 1% by weight, more preferably from 0.2 to 0.6% by weight, and even more preferably from 0.3 to 0.5% by weight, of the dental composition for oral use of the present invention, from the viewpoint of obtaining a masking effect to a foreign taste of a cationic bactericidal agent.

The nonionic surfactant includes, sugar fatty acid esters, polyglycerol fatty acid esters, polyoxyethylene hydrogenated castor oil, sorbitan fatty acid esters, polyoxyethylene polyoxypropylene block copolymer-type nonionic surfactants, fatty acid alkanolamides, polyoxyethylene fatty acid esters, fatty acid monoglycerides, polyoxyethylene alkyl ethers, and the like. Among them, it is preferable that the nonionic surfactant includes a polyglycerol fatty acid ester, a sucrose fatty acid ester, a maltose fatty acid ester, or a lactose fatty acid ester, from the viewpoint of suppressing the formation of dental plaques. It is desired that each of these nonionic surfactants is contained in an amount of preferably from 0.01 to 2% by weight, more preferably from 0.05 to 1% by weight, and even more preferably from 0.1 to 0.8% by weight, of the dental composition for oral use of the present invention, from the viewpoint of solubilizing the components such as a hardly water-soluble bactericidal agent or a pharmaceutically effective agent, thereby consequently exhibiting detaining effects of pharmaceutical components and at the same time providing the purpose of excellent storage stability (external appearance stability) and taste.

The anionic surfactant includes alkyl sulfuric esters, such as sodium lauryl sulfate and sodium myristyl sulfate; N-acylamino acid salts, such as lauroylsarcosine sodium; acyl taurine salts, such as lauroyl methyltaurine sodium; sulfonates of fatty acids, such as sodium ethyl coconut oil fatty acid sulfonic esters; and the like.

It is preferable that each of these anionic surfactants is contained in an amount of 0.01% by weight or less, i.e. 0 to 0.01% by weight, of the dental composition for oral use, from the viewpoint of irritation, adsorption of the cationic bactericidal agent to the teeth, and the like.

The viscosity adjusting agent includes cellulose derivatives such as carboxymethyl cellulose sodium and hydroxyethyl cellulose; alginic acid derivatives, such as sodium alginate and propylene glycol alginate; gums such as carrageenan, xanthane gum, gellan gum, tragacanth gum, and karaya gum; synthetic binding agents such as polyvinyl alcohol, sodium polyacrylate and vinyl carboxylate polymers; inorganic binding agents, such as AEROSIL (highly dispersible silica), VEEGUM, and LAPONITE; starch degradation products, such as dextrin and reducing dextrin; and the like. These viscosity adjusting agents can be used singly or in a mixture of two or more kinds. It is desired that each of these viscosity adjusting agents is contained in an amount of preferably from 0.001 to 10% by weight, more preferably from 0.01 to 5% by weight, and even more preferably from 0.1 to 5% by weight, of the dental composition for oral use of the present invention, from the viewpoint of formulating the viscosity adjusting agent within the range that would not hinder the effects of the present invention.

The polyhydric alcohol includes propylene glycol, glycerol, polyethylene glycol, and the like. It is desired that each of these polyhydric alcohols is contained in an amount of preferably from 0 to 30% by weight, more preferably from 2 to 20% by weight, and even more preferably from 5 to 15% by weight, of the dental composition for oral use of the present invention, from the viewpoint of feel of use and storage stability. The buffering agent includes phthalic acid, phosphoric acid, citric acid, succinic acid, acetic acid, fumaric acid, malic acid, and carbonic acid, and potassium salts, sodium salts, and ammonium salts thereof, amino acids and salts thereof, ribonucleic acids and salts thereof, and further sodium hydroxide, borax, hydrogencarbonates, and the like. Each of these buffering agents can be formulated singly or in a combination of two or more kinds so as to have a pH of the liquid composition for oral use of the present invention of preferably within the range of from 4 to 9, and it is desired that the buffering agent is contained in an amount of preferably from 0.0001 to 5% by weight, more preferably from 0.001 to 1% by weight, and even more preferably from 0.01 to 0.5% by weight. The sweetener includes saccharin sodium, acesulfame potassium, stevioside, neohesperidyl dihydrochalcone, glycyrrhizin, perillartine, thaumatin, asparatyl phenylalanyl methyl ester, sucralose, and the like. It is desired that each of these sweeteners is contained in an amount of preferably from 0.001 to 5.0% by weight, more preferably from 0.005 to 1.0% by weight, and even more preferably from 0.01 to 0.5% by weight, of the dental composition for oral use of the present invention, from the viewpoint of formulating the sweetener within the range that would not hinder the effects of the present invention.

Other pharmaceutically effective agent includes one or more compounds selected from antiplasmin agents such as tranexamic acid and epsilon($\epsilon$)-aminocaproic acid; vitamins such as ascorbic acid and tocopherol ester; glycyrrylitinates; allantoins; plant extracts from *Phellodendron amurense, Scutellaria baicalensis* root, *Matricaria chamomilla* flower, *Krameria triandra* root, and *Commiphora myrrha*, or the like; enzymes such as dextranase, mutanase, and lysozyme chloride; salts such as sodium chloride, potassium nitrate, carbonates, bicarbonates, and sesquicarbonates; sodium copper chlorophyllin, copper gluconate, zinc chloride, zeolite, water-soluble inorganic phosphoric acid compounds, aluminum lactate, and the like. Although the amount of these other pharmaceutically effective agents differs depending upon the compounds, it is desired that each of these pharmaceutically effective agent is contained in an amount of preferably from 0.001 to 5.0% by weight, more preferably from 0.01 to 5.0% by weight, and even more preferably from 0.01 to 3.0% by weight, of the dental composition for oral use of the present invention, from the viewpoint of enhancing stability and an effect of suppressing dental caries.

The colorant includes legal dyes such as Red No. 1, Red No. 3, Red No. 105, Yellow No. 4, Yellow No. 203, Blue No. 1, Blue No. 2, Green No. 3, and Green No. 201, and pigments such as titanium oxide and ultramarine. These colorants can be formulated singly or in a combination of two or more kinds. Although the amount of each of these colorants formulated is not particularly limited, it is desired that each of these colorants is contained in an amount of preferably from 0.00001 to 2.0% by weight, more preferably from 0.0001 to 1.0% by weight, and even more preferably from 0.0001 to 0.1% by weight, of the dental composition for oral use of the present invention, from the viewpoint of aesthetic appreciation.

In addition, the dental composition for oral use of the present invention suitably contains a water-soluble metal fluoride such as sodium fluoride, sodium monofluorophosphate, or stannous fluoride. If a metal fluoride as mentioned above is contained, fluorine ions are incorporated into the dentine upon contacting the dental composition for oral use of the present invention with surfaces of the teeth, so that fluoroapatite is formed on the surfaces of the teeth, whereby an effect of enhancing anti-caries formation of the teeth can be expected. Each of these metal fluorides is contained in the dental composition for oral use of the present invention in an amount, as calculated as fluorine ions, of preferably from 0.1 to 5000 ppm based on the entire amount of the composition. When the metal fluoride is contained in an amount of less than 0.1 ppm, there is a risk of not sufficiently obtaining an effect of enhancing anti-caries formation, and when the metal fluoride is contained in an amount exceeding 5000 ppm, there is a risk in causing some problems in safety when mistakenly taken in larger amounts.

The dental composition for oral use of the present invention is not particularly limited, so long as the composition contains a phosphorylated saccharide (a), a polyphosphoric acid and/or a salt thereof (b), and a cationic bactericidal agent (c) in a given proportion, and the dental composition for oral use can be easily produced by a known method by one of ordinary skill in the art.

EXAMPLES

The present invention will be specifically described hereinbelow by the Examples, without intending to limit the scope of the present invention thereto.

Production Example 1

(Synthesis of Phosphorylated Pullulan)

In a separable flask having an inner volume of 2 L, 40.0 g of pullulan (manufactured by HAYASHIBARA SHOJI, INC.) was dissolved in 200 mL of distilled water at room temperature. While stirring this solution, 1000 g of a 1 M aqueous phosphoric acid solution, of which pH was adjusted with sodium hydroxide to 5.5, was added over 10 minutes. After the addition, the stirring was continued for an additional 1 hour. Thereafter, the distilled water was distilled off in a volume of about 1100 mL at a temperature between 100° and 103° C., the stirring was then continued at 170° C. for 3 hours, and the reaction product was cooled to room temperature. The reaction product was taken out and pulverized with a mortar and pestle, to give 98.4 g of a brown solid.

Ninety grams of the brown solid obtained above was dissolved in 1500 mL of distilled water. While stirring this solution, 1500 mL of 99.5% ethanol was added to the solution over 10 minutes. Concurrently with the addition, the formation of the precipitates was confirmed. After the termination of the addition, the mixture was continued stirring for an additional 1 hour. The mixture was then allowed to stand to separate into layers, and the supernatant was removed by decantation. Thereafter, residual precipitates were dissolved again in 1500 mL of distilled water, and 1500 mL of 99.5% ethanol was added to the solution over 10 minutes, and the precipitates were collected. The above-mentioned procedures were carried out twice, the precipitates were then dissolved in distilled water (400 mL), and 99.5% ethanol (2000 mL) was added gradually thereto in a small amount over 5 minutes while stirring the solution. The sedimented precipitates were collected by filtration with a Kiriyama filter (3G), washed with 99.5% ethanol (500 mL), and dried at 60° C. under a reduced pressure for 12 hours, to give 28.5 g of a slightly brownish white solid. Further, 25 g of this white solid was dissolved in distilled water, and this solution was applied to a miniaturized bench-top electrodialyzer (Micro Acilyzer S3, manufactured by SUNACTIS), thereby obtaining 13 g of phosphorylated pullulan in the form of a transparent, pale brown solid.

The solid obtained was subjected to an IR spectroscopy (FTIR-8200PC, manufactured by Shimadzu Corporation) (KBr tablet method). As a result, peaks ascribed to the phosphoric acid group site were observed at 1000 to 1200 $cm^{-1}$. In addition, $^{31}$P-NMR (JNM-LA500, manufactured by JEOL, Ltd.) was measured, and as a result, a signal ascribed to phosphorus forming a phosphoric ester bonding to pullulan was obtained at 2 to 5 ppm. The solid was subjected to an elemental analysis of phosphorus atom according to ICP emission spectroscopy (IRIS-AP, manufactured by Jarrel-Ash). From the results, it was judged that about 2.6% of the hydroxyl groups of the pullulan had undergone phosphorylation. In addition, the solid was further subjected to GPC analysis (column: TSK gel α-M (manufactured by Tosoh Corporation), mobile phase: 0.1 M-aqueous NaCl solution). As a result, the solid had a number-average molecular weight (Mn) of 24,000.

Production Example 2

(Synthesis of Phosphorylated Mannan)

The same procedures as in Production Example 1 were carried out using mannan (RHEOLEX LM, manufactured by SHIMIZU CHEMICAL CORPORATION) as a raw material in place of pullulan, to synthesize phosphorylated mannan.

About 2.3% of the hydroxyl groups of mannan had undergone phosphorylation, and the phosphorylated mannan had a number-average molecular weight (Mn) of 13,000.

Production Example 3

(Synthesis of Phosphorylated Maltodextrin)

The same procedures as in Production Example 1 were carried out using maltodextrin (Pinedex-2, manufactured by Matsutani Chemical Industry Co., Ltd.) as a raw material in place of pullulan, to synthesize phosphorylated maltodextrin. About 2.8% of the hydroxyl groups of maltodextrin had undergone phosphorylation, and the phosphorylated maltodextrin had a number-average molecular weight (Mn) of 1,400.

(Glucose-6-Phosphoric Acid)

As glucose-6-phosphoric acid, a product manufactured by Aldrich was directly used.

(Sodium Pyrophosphate)

As sodium pyrophosphate, a product manufactured by Wako Pure Chemical Industries, Ltd. was directly used.

(Cetyl Pyridinium Chloride)

As cetyl pyridinium chloride, a product manufactured by Aldrich was directly used.

(Benzethonium Chloride)

As benzethonium chloride, a product manufactured by Wako Pure Chemical Industries, Ltd. was directly used.

Example 1

A solution prepared by dissolving 0.5 g of cetyl pyridinium chloride (hereinafter referred to as "CPC") as a cationic bactericidal agent, 0.8 g of the phosphorylated pullulan synthesized in Production Example 1 mentioned above as a phosphorylated saccharide, and 0.2 g of sodium pyrophosphate as a polyphosphoric acid in 10 g of water was diluted 100-folds with water, to prepare a composition containing the CPC in an amount of 0.05% by weight, the phosphorylated pullulan in an amount of 0.08% by weight, the sodium pyrophosphate in an amount of 0.02% by weight, and water in an amount of 99.85% by weight, to provide a composition of Example 1.

Example 2

The same procedures as in Example 1 were carried out using the CPC as a cationic bactericidal agent, the phosphorylated mannan synthesized in Production Example 2 mentioned above as a phosphorylated saccharide, and the sodium pyrophosphate as a polyphosphoric acid, to prepare a composition, to provide a composition of Example 2.

Example 3

The same procedures as in Example 1 were carried out using the CPC as a cationic bactericidal agent, the phosphorylated maltodextrin synthesized in Production Example 3 mentioned above as a phosphorylated saccharide, and the sodium pyrophosphate as a polyphosphoric acid, to prepare a composition, to provide a composition of Example 3.

Example 4

The same procedures as in Example 1 were carried out using the CPC as a cationic bactericidal agent, the glucose-6-phosphoric acid as a phosphorylated saccharide, and the sodium pyrophosphate as a polyphosphoric acid, to prepare a composition, to provide a composition of Example 4.

Examples 5 to 22

The same procedures as in Example 1 were carried out using the CPC in an amount of 0.5 g as a bactericidal agent, the phosphorylated pullulan synthesized in Production Example 1 as a phosphorylated saccharide, and the sodium pyrophosphate as a polyphosphoric acid, while varying the amounts of the phosphorylated pullulan and the sodium pyrophosphate formulated, respectively, to prepare compositions, to provide compositions of Examples 5 to 22.

Example 23

A solution prepared by dissolving 0.1 g of benzethonium chloride (hereinafter referred to as "BTC") as a cationic bactericidal agent, 0.1 g of the phosphorylated pullulan synthesized in Production Example 1 as a phosphorylated saccharide, and 0.1 g of the sodium pyrophosphate as a polyphosphoric acid in 10 g of water was diluted 100-folds with water, to prepare a composition containing the BTC in an amount of 0.01% by weight, the phosphorylated pullulan in an amount of 0.01% by weight, the sodium pyrophosphate in an amount of 0.01% by weight, and water in an amount of 99.97% by weight, to provide a composition of Example 23.

Example 24

The same procedures as in Example 23 were carried out using the BTC as a bactericidal agent, the phosphorylated mannan synthesized in Production Example 2 mentioned above as a phosphorylated saccharide, and the sodium pyrophosphate as a polyphosphoric acid, to prepare a composition, to provide a composition of Example 24.

Example 25

The same procedures as in Example 23 were carried out using the BTC as a bactericidal agent, the phosphorylated maltodextrin synthesized in Production Example 3 mentioned above as a phosphorylated saccharide, and the sodium pyrophosphate as a polyphosphoric acid, to prepare a composition, to provide a composition of Example 25.

Example 26

The same procedures as in Example 23 were carried out using the BTC as a bactericidal agent, the glucose-6-phosphoric acid as a phosphorylated saccharide, and the sodium pyrophosphate as a polyphosphoric acid, to prepare a composition, to provide a composition of Example 26.

Examples 27 to 29

The same procedures as in Example 23 were carried out using the BTC in an amount of 0.1 g as a bactericidal agent, the phosphorylated pullulan synthesized in Production Example 1 as a phosphorylated saccharide, and the sodium pyrophosphate as a polyphosphoric acid, while varying the amounts of the phosphorylated pullulan and the sodium pyrophosphate formulated, respectively, to prepare compositions, to provide compositions of Examples 27 to 29.

Example 30

A solution prepared by dissolving 0.2 g of the CPC as a cationic bactericidal agent, 0.1 g of the phosphorylated pullulan synthesized in Production Example 1 mentioned above as a phosphorylated saccharide, and 0.1 g of the sodium pyrophosphate as a polyphosphoric acid in 10 g of water was diluted 100-folds with water, to prepare a composition containing the CPC in an amount of 0.02% by weight, the phosphorylated pullulan and the sodium pyrophosphate, each in an amount of 0.01% by weight, and water in an amount of 99.96% by weight, to provide a composition of Example 30.

Example 31

A solution prepared by dissolving 0.2 g of the CPC as a cationic bactericidal agent, 0.1 g of the phosphorylated pullulan synthesized in Production Example 1 mentioned above as a phosphorylated saccharide, and 0.1 g of the sodium pyrophosphate as a polyphosphoric acid in 10 g of water was diluted 10-folds with water, to prepare a composition containing the CPC in an amount of 0.2% by weight, the phosphorylated pullulan and the sodium pyrophosphate, each in an amount of 0.1% by weight, and water in an amount of 99.6% by weight, to provide a composition of Example 31.

Example 32

A solution prepared by dissolving 0.1 g of the CPC as a cationic bactericidal agent, 0.1 g of the phosphorylated pullulan synthesized in Production Example 1 mentioned above as a phosphorylated saccharide, and 0.1 g of the sodium pyrophosphate as a polyphosphoric acid in 10 g of water was diluted 100-folds with water, to prepare a composition containing the CPC, the phosphorylated pullulan and the sodium pyrophosphate, each in an amount of 0.01% by weight, and water in an amount of 99.97% by weight, to provide a composition of Example 32.

Example 33

A solution prepared by dissolving 0.1 g of the CPC as a cationic bactericidal agent, 0.08 g of the phosphorylated pullulan synthesized in Production Example 1 mentioned above as a phosphorylated saccharide, and 0.02 g of the sodium pyrophosphate as a polyphosphoric acid in 10 g of water was diluted 100-folds with water, to prepare a composition containing the CPC in an amount of 0.01% by weight, the phosphorylated pullulan in an amount of 0.008% by weight, and the sodium pyrophosphate in an amount of 0.002% by weight, and water in an amount of 99.98% by weight, to provide a composition of Example 33.

Example 34

The same procedures as in Example 30 were carried out using the CPC as a bactericidal agent, the phosphorylated mannan synthesized in Production Example 2 as a phosphorylated saccharide, and the sodium pyrophosphate as a polyphosphoric acid, to prepare a composition, to provide a composition of Example 34.

Example 35

The same procedures as in Example 30 were carried out using the CPC as a bactericidal agent, the phosphorylated maltodextrin synthesized in Production Example 3 as a phosphorylated saccharide, and the sodium pyrophosphate as a polyphosphoric acid, to prepare a composition, to provide a composition of Example 35.

Example 36

The same procedures as in Example 30 were carried out using the CPC as a bactericidal agent, the glucose-6-phosphoric acid as a phosphorylated saccharide, and the sodium pyrophosphate as a polyphosphoric acid, to prepare a composition, to provide a composition of Example 36.

Comparative Example 1

A solution prepared by dissolving 0.5 g of the CPC as a bactericidal agent in 10 g of water was diluted 100-folds with water, to prepare a composition containing the CPC in an amount of 0.05% by weight and water in an amount of 99.95% by weight, to provide a composition of Comparative Example 1.

Comparative Example 2

A solution prepared by dissolving 0.1 g of the BTC as a bactericidal agent in 10 g of water was diluted 100-folds with water, to prepare a composition containing the BTC in an amount of 0.01% by weight and water in an amount of 99.99% by weight, to provide a composition of Comparative Example 2.

Comparative Example 3

A solution prepared by dissolving 0.5 g of the CPC as a bactericidal agent and 0.5 g of the phosphorylated pullulan synthesized in Production Example 1 as a phosphorylated saccharide in 10 g of water was diluted 100-folds with water, to prepare a composition containing the CPC and the phosphorylated pullulan each in an amount of 0.05% by weight, and water in an amount of 99.90% by weight, to provide a composition of Comparative Example 3.

Comparative Example 4

A solution prepared by dissolving 0.1 g of the BTC as a bactericidal agent and 0.1 g of the phosphorylated pullulan synthesized in Production Example 1 as a phosphorylated saccharide in 10 g of water was diluted 100-folds with water, to prepare a composition containing the BTC and the phosphorylated pullulan each in an amount of 0.01% by weight, and water in an amount of 99.98% by weight, to provide a composition of Comparative Example 4.

Comparative Examples 5 and 6

The same procedures as in Comparative Example 3 were carried out using the CPC in an amount of 0.5 g as a bactericidal agent and the phosphorylated pullulan synthesized in Production Example 1 as a phosphorylated saccharide, while varying the amounts of the phosphorylated pullulan formulated, to prepare compositions, to provide compositions of Comparative Examples 5 and 6.

Comparative Example 7

A solution prepared by dissolving 0.5 g of the CPC as a bactericidal agent and 0.5 g of the sodium pyrophosphate as a polyphosphoric acid in 10 g of water was diluted 100-folds with water, to prepare a composition containing the CPC and the sodium pyrophosphate each in an amount of 0.05% by weight, and water in an amount of 99.90% by weight, to provide a composition of Comparative Example 7.

Comparative Examples 8 and 9

The same procedures as in Comparative Example 7 were carried out using the CPC in an amount of 0.5 g as a bactericidal agent and sodium pyrophosphate as a polyphosphoric acid, while varying the amounts of the sodium pyrophosphate formulated, to prepare compositions, to provide compositions of Comparative Examples 8 and 9.

Comparative Examples 10 and 11

The CPC as a bactericidal agent, the phosphorylated pullulan synthesized in Production Example 1 as a phosphorylated saccharide, and the sodium pyrophosphate as a polyphosphoric acid were used in amounts so that the amounts formulated were as listed in Table 1 to prepare compositions, to provide compositions of Comparative Examples 10 and 11.

Comparative Example 12

A solution prepared by dissolving 0.1 g of the CPC as a bactericidal agent in 10 g of water was diluted 100-folds with water, to prepare a composition containing the CPC in an amount of 0.01% by weight and water in an amount of 99.99% by weight, to provide a composition of Comparative Example 12.

Comparative Example 13

A solution prepared by dissolving 0.1 g of the CPC as a bactericidal agent and 0.1 g of the sodium pyrophosphate as a polyphosphoric acid in 10 g of water was diluted 100-folds with water, to prepare a composition containing the CPC and the sodium pyrophosphate each in an amount of 0.01% by weight, and water in an amount of 99.98% by weight, to provide a composition of Comparative Example 13.

Comparative Example 14

A solution prepared by dissolving 0.1 g of the CPC as a bactericidal agent and 0.1 g of the phosphorylated pullulan synthesized in Production Example 1 as a phosphorylated saccharide in 10 g of water was diluted 100-folds with water, to prepare a composition containing the CPC and the phosphorylated pullulan each in an amount of 0.01% by weight, and water in an amount of 99.98% by weight, to provide a composition of Comparative Example 14.

Test Example [Adhesion Test of Bacteria to Surfaces of Teeth]

As a test method for evaluating an effect of suppressing bacterial adhesion to surfaces of the teeth, the evaluation was made by previously applying any one of the compositions of Examples 1 to 36 or Comparative Examples 1 to 14 to a synthetic apatite surface, and observing the amount of adhesion of S. mutans on this surface with an electron microscope. Concrete procedures are as follows.

(1) Culture of S. Mutans

As a bacterium in the oral cavity, Streptococcus mutans 854S (S. mutans), a bacterium causative of dental caries, was used. S. mutans is cultured at 37° C. under aerobic conditions using a medium (TSBY) in which 0.5% by weight yeast extract (Bacto™ Yeast Extract; manufactured by Becton, Dickinson and Company) is added to a tryptic soy broth (Bacto™ Tryptic Soy Broth: Soybean-Casein Digest Medium; manufactured by Becton, Dickinson and Company). Here, upon the formation of a biofilm on S. mutans, one prepared by adding 5% by weight sucrose to the TSBY is used as a medium. S. mutans is cultured to a logarithmic growth phase. Thereafter, the absorbance is determined (SPECTRONIC 20A, manufactured by SPECTRONIC) at a wavelength of 570 nm, and a suspension of S. mutans is prepared using a medium in which 5% by weight sucrose is added to the TSBY so as to have a concentration of $1 \times 10^5$ cfu/mL.

(2) Treatment to Apatite Surfaces

Four milliliters of any one of the compositions of Examples 1 to 36 or Comparative Examples 1 to 14 is taken into a cylindrical vessel having a diameter of 22 mm and a depth of 17.5 mm, and an apatite test plate (10 mm×10 mm×2 mm, manufactured by PENTAX Corporation, apatite pellet APP-101, the surface being mirror-polished) is immersed into the cylindrical vessel. The apatite test plate is immersed at 37° C. for 1 hour, and an apatite test plate is then taken out into a fresh cylindrical vessel, and immersed in distill water and washed twice, and the washed test plate is air-dried.

(3) Proliferation of S. Mutans on Apatite Surface

Four milliliters of the suspension of S. mutans prepared in accordance with the method of the above (1) is poured into a cylindrical vessel having a diameter of 22 mm and a depth of 17.5 mm, and an apatite test plate treated with any one of the compositions of Examples 1 to 36 or Comparative Examples 1 to 14 is immersed therein according to the method of the above (2). The cells are cultured at 37° C. for 12 hours under aerobic conditions, the apatite test plate is then taken out, and S. mutans adhered to this surface is observed with a scanning electron microscope (SEM) in accordance with the following procedures to observe the state of proliferation.

(4) Electron Microscope Observation of S. Mutans on Apatite Surface

Sodium cacodylate (manufactured by Wako Pure Chemical Industries, Ltd.) in an amount of 0.01 mol and sodium chloride in an amount of 0.15 mol are dissolved in 1 liter of distilled water, to prepare a cacodylate buffer (pH 7.0±0.2). The apatite test plate after being cultured as described in the above (3) is immersed in the cacodylate buffer previously warmed to 37° C., and allowed to stand therein for 10 minutes. The procedures are carried out twice, and the apatite test plate is washed.

The test plate after being washed is immersed in an immobilization solution (solution containing 1% glutaraldehyde, 0.01 M sodium cacodylate, and 0.15 M NaCl), and allowed to stand for 10 minutes. Thereafter, the test plate is taken out from the immobilization solution, and immersed again in a fresh similar immobilization solution, and allowed to stand for 30 minutes to immobilize S. mutans.

The test plate is transferred to a fresh cacodylate buffer and immersed for 15 minutes to wash, and the washing procedures are repeated twice. Subsequently, the test plate is immersed sequentially in 50% ethanol, 70% ethanol, 90% ethanol, and 95% ethanol (volume ratio) for 15 minutes each, and finally an immersion procedure in 100% ethanol is repeated twice, and dehydrated (15 minutes each).

Next, this test plate is immersed 4 times in t-butanol for 15 minutes. The test plate is dried with a critical point dryer (ES-2030, manufactured by Hitachi Ltd.), the test plate obtained is subjected to Pt—Pd coating with an ion sputter (E-1010, manufactured by HITACHI LTD.), to prepare a test plate for the SEM observation, and the test plate is observed with an SEM (S-3500N, manufactured by HITACHI LTD.).

(5) Evaluation of the Amount of Bacteria Adhesion

The amount of bacteria adhesion was evaluated by taking an SEM photograph on any 5 spots on the apatite test plate (size of photograph 20 μm×25 μm), subjecting each photograph to imaging analysis, and calculating a proportion of the area to which the bacteria are adhered to the area of the entire photograph, and the evaluation is made by the following criteria.

◉: the area being less than 10%;
○: the area being 10% or more and less than 50%;
Δ: the area being 50% or more and less than 80%; and
×: the area being 80% or more.

The amount of bacteria adhesion in Examples 1 to 36 and Comparative Examples 1 to 14 are shown in Tables 1 to 3.

TABLE 1

| Component (% by wt.) Ex. No. | (a) Phosphorylated Pullulan | (a) Phosphorylated Mannan | (a) Phosphorylated Maltodextrin | (a) Glucose-6-phosphoric acid | (b) Sodium Pyrophosphate | (c) CPC | (c) BTC | (d) Water | Total (% by wt.) | [(a)+(b)]/(c) | (a)/(b) | Amount of Bacteria Adhesion |
|---|---|---|---|---|---|---|---|---|---|---|---|---|
| 1  | 0.08   | —    | —    | —    | 0.02   | 0.05 | — | Bal. | 100 | 2    | 4    | ◉ |
| 2  | —      | 0.08 | —    | —    | 0.02   | 0.05 | — | Bal. | 100 | 2    | 4    | ◉ |
| 3  | —      | —    | 0.08 | —    | 0.02   | 0.05 | — | Bal. | 100 | 2    | 4    | ◉ |
| 4  | —      | —    | —    | 0.08 | 0.02   | 0.05 | — | Bal. | 100 | 2    | 4    | ○ |
| 5  | 0.8    | —    | —    | —    | 0.2    | 0.05 | — | Bal. | 100 | 20   | 4    | ○ |
| 6  | 0.2    | —    | —    | —    | 0.8    | 0.05 | — | Bal. | 100 | 20   | 0.25 | ○ |
| 7  | 0.4    | —    | —    | —    | 0.1    | 0.05 | — | Bal. | 100 | 10   | 4    | ◉ |
| 8  | 0.1    | —    | —    | —    | 0.4    | 0.05 | — | Bal. | 100 | 10   | 0.25 | ◉ |
| 9  | 0.2    | —    | —    | —    | 0.05   | 0.05 | — | Bal. | 100 | 5    | 4    | ◉ |
| 10 | 0.125  | —    | —    | —    | 0.125  | 0.05 | — | Bal. | 100 | 5    | 1    | ◉ |
| 11 | 0.05   | —    | —    | —    | 0.2    | 0.05 | — | Bal. | 100 | 5    | 0.25 | ◉ |
| 12 | 0.09   | —    | —    | —    | 0.01   | 0.05 | — | Bal. | 100 | 2    | 9    | ◉ |
| 13 | 0.01   | —    | —    | —    | 0.09   | 0.05 | — | Bal. | 100 | 2    | 0.11 | ◉ |
| 14 | 0.0225 | —    | —    | —    | 0.0025 | 0.05 | — | Bal. | 100 | 0.5  | 9    | ◉ |
| 15 | 0.02   | —    | —    | —    | 0.005  | 0.05 | — | Bal. | 100 | 0.5  | 4    | ◉ |
| 16 | 0.0125 | —    | —    | —    | 0.0125 | 0.05 | — | Bal. | 100 | 0.5  | 1    | ◉ |
| 17 | 0.0025 | —    | —    | —    | 0.0225 | 0.05 | — | Bal. | 100 | 0.5  | 0.11 | ◉ |
| 18 | 0.008  | —    | —    | —    | 0.002  | 0.05 | — | Bal. | 100 | 0.2  | 4    | ◉ |
| 19 | 0.002  | —    | —    | —    | 0.008  | 0.05 | — | Bal. | 100 | 0.2  | 0.25 | ◉ |
| 20 | 0.004  | —    | —    | —    | 0.001  | 0.05 | — | Bal. | 100 | 0.10 | 4    | ◉ |

TABLE 2

| Component (% by wt.) Ex. No. | (a) Phosphorylated Pullulan | (a) Phosphorylated Mannan | (a) Phosphorylated Maltodextrin | (a) Glucose-6-phosphoric acid | (b) Sodium Pyrophosphate | (c) CPC | (c) BTC | (d) Water | Total (% by wt.) | [(a)+(b)]/(c) | (a)/(b) | Amount of Bacteria Adhesion |
|---|---|---|---|---|---|---|---|---|---|---|---|---|
| 21 | 0.001   | —    | —    | —    | 0.004   | 0.05 | —    | Bal. | 100 | 0.10 | 0.25 | ○ |
| 22 | 0.00125 | —    | —    | —    | 0.00125 | 0.05 | —    | Bal. | 100 | 0.05 | 1    | ○ |
| 23 | 0.01    | —    | —    | —    | 0.01    | —    | 0.01 | Bal. | 100 | 2    | 1    | ◉ |
| 24 | —       | 0.01 | —    | —    | 0.01    | —    | 0.01 | Bal. | 100 | 2    | 1    | ◉ |
| 25 | —       | —    | 0.01 | —    | 0.01    | —    | 0.01 | Bal. | 100 | 2    | 1    | ◉ |
| 26 | —       | —    | —    | 0.01 | 0.01    | —    | 0.01 | Bal. | 100 | 2    | 1    | ○ |
| 27 | 0.008   | —    | 0    | —    | 0.002   | —    | 0.01 | Bal. | 100 | 1    | 4    | ◉ |
| 28 | 0.005   | —    | 0    | —    | 0.005   | —    | 0.01 | Bal. | 100 | 1    | 1    | ◉ |
| 29 | 0.002   | —    | 0    | —    | 0.008   | —    | 0.01 | Bal. | 100 | 1    | 0.25 | ◉ |
| 30 | 0.01    | —    | 0    | —    | 0.01    | 0.02 | —    | Bal. | 100 | 1    | 1    | ◉ |
| 31 | 0.1     | —    | 0    | —    | 0.1     | 0.2  | —    | Bal. | 100 | 1    | 1    | ◉ |
| 32 | 0.01    | —    | 0    | —    | 0.01    | 0.01 | —    | Bal. | 100 | 2    | 1    | ◉ |
| 33 | 0.008   | —    | 0    | —    | 0.002   | 0.01 | —    | Bal. | 100 | 1    | 4    | ◉ |
| 34 | —       | 0.01 | 0    | —    | 0.01    | 0.02 | —    | Bal. | 100 | 1    | 1    | ◉ |
| 35 | —       | —    | 0.01 | —    | 0.01    | 0.02 | —    | Bal. | 100 | 1    | 1    | ◉ |
| 36 | —       | —    | —    | 0.01 | 0.01    | 0.02 | —    | Bal. | 100 | 1    | 1    | ○ |

TABLE 3

| Component (% by wt.) Comp. Ex. No. | Phosphorylated Pullulan | Phosphorylated Mannan | Phosphorylated Maltodextrin | Glucose-6-phosphoric acid | (b) Sodium Pyrophosphate | (c) CPC | (c) BTC | (d) Water | Total (% by wt.) | [(a)+(b)]/(c) | (a)/(b) | Amount of Bacteria Adhesion |
|---|---|---|---|---|---|---|---|---|---|---|---|---|
| 1 | — | — | — | — | — | 0.05 | — | Bal. | 100 | 0 | — | X |
| 2 | — | — | — | — | — | — | 0.01 | Bal. | 100 | 0 | — | X |
| 3 | 0.05 | — | — | — | — | 0.05 | — | Bal. | 100 | 1 | — | Δ |
| 4 | 0.01 | — | — | — | — | — | 0.01 | Bal. | 100 | 1 | — | Δ |
| 5 | 0.5 | — | — | — | — | 0.05 | — | Bal. | 100 | 10 | — | Δ |
| 6 | 0.01 | — | — | — | — | 0.05 | — | Bal. | 100 | 0.2 | — | Δ |
| 7 | — | — | — | — | 0.05 | 0.05 | — | Bal. | 100 | 1 | — | X |
| 8 | — | — | — | — | 0.5 | 0.05 | — | Bal. | 100 | 10 | — | X |
| 9 | — | — | — | — | 0.01 | 0.05 | — | Bal. | 100 | 0.2 | — | X |
| 10 | 0.00075 | — | — | — | 0.00075 | 0.05 | — | Bal. | 100 | 0.03 | 1 | X |
| 11 | 0.525 | — | — | — | 0.525 | 0.05 | — | Bal. | 100 | 21 | 1 | X |
| 12 | — | — | — | — | — | 0.01 | — | Bal. | 100 | 0 | — | X |
| 13 | — | — | — | — | 0.01 | 0.01 | — | Bal. | 100 | 1 | 1 | X |
| 14 | 0.01 | — | — | — | — | 0.01 | — | Bal. | 100 | 1 | 1 | Δ |

From Examples 1 to 36, hardly any bacteria were adhered to the apatite surface that was surface-treated with a composition in which the phosphorylated saccharide, the sodium polyphosphate, and the cationic bactericidal agent were used together.

By contrast, the adhesion of the bacteria was markedly observed in the compositions of the CPC alone (Comparative Examples 1 and 12), the BTC alone (Comparative Example 2), and the compositions in which the sodium pyrophosphate and the CPC were used in combination (Comparative Examples 7 to 9 and 13). In addition, the adhesion of the bacteria was observed in the compositions in which the phosphorylated pullulan and the CPC were used in combination (Comparative Examples 3, 5, 6, and 14) and the compositions in which the phosphorylated pullulan and the BTC were used in combination (Comparative Example 4).

As described above, it was shown that the dental composition for oral use of the present invention can suppress adhesion of bacteria in the oral cavity to surfaces of the teeth for a long period of time by using a cationic bactericidal agent together with a phosphorylated saccharide and a polyphosphoric acid.

INDUSTRIAL APPLICABILITY

The dental composition for oral use of the present invention can be suitably used for an oral cavity cleaning agent or the like. The oral cavity cleaning agent includes, for example, dentifrice agents such as a paste dentifrice agent, a powder dentifrice agent, and a liquid dentifrice agent, a mouse-wash agent, a troche, a tablet, a cream, an ointment, a bonding agent, a mouth spray, a coating agent to tooth surface or a dental prosthetic, a hypersensitive inhibitor, a therapeutic agent for periodontal diseases, that is applied to a periodontal pocket, wet tissue for oral cavity care, an oral refreshing agent, chewing gum, or a gargling agent, or the like.

The invention claimed is:

1. A dental composition for oral use, comprising at least one of a phosphorylated saccharide selected from the group consisting of phosphorylated pullulan and a phosphorylated mannan (a), a polyphosphoric acid and/or a salt thereof (b), and a cationic bactericidal agent (c), wherein a ratio of a total amount of the phosphorylated saccharide (a) and the polyphosphoric acid and/or a salt thereof (b) contained to an amount of the cationic bactericidal agent (c) contained, i.e. {(a)+(b)}/(c), is from 0.05 to 20 in a weight ratio,
   wherein the phosphorylated saccharide is a phosphorylated polysaccharide, of which number-average molecular weight Mn is within the range of from 1,000 to 100,000,
   wherein the phosphorylated saccharide has hydroxyl groups that are phosphorylated in an amount of 0.5 to 10% by number of hydroxyl groups of the saccharide,
   wherein the phosphorylated saccharide (a) and the polyphosphoric acid and/or a salt thereof (b) are present in an amount such that a ratio of A/B is 0.02 to 50, and
   wherein the dental composition provides an inhibition of bacterial adhesion to an apatite test plate analyzed by scanning electron microscopy.

2. The dental composition for oral use according to claim 1, further comprising a solvent (d).

3. The dental composition for oral use according to claim 1, wherein the phosphorylated saccharide (a) is contained in an amount of from 0.001 to 10% by weight, the polyphosphoric acid and/or a salt thereof (b) is contained in an amount of from 0.001 to 10% by weight, and the cationic bactericidal agent (c) is contained in an amount of from 0.0001 to 5% by weight.

4. The dental composition for oral use according to claim 1, wherein the dental composition for oral use is an oral cavity cleaning agent.

5. The dental composition for oral use according to claim 2, wherein the phosphorylated saccharide (a) is contained in an amount of from 0.001 to 10% by weight, the polyphosphoric acid and/or a salt thereof (b) is contained in an amount of from 0.001 to 10% by weight, and the cationic bactericidal agent (c) is contained in an amount of from 0.0001 to 5% by weight.

6. The dental composition for oral use according to claim 2, wherein the dental composition for oral use is an oral cavity cleaning agent.

* * * * *